United States Patent
Chisholm et al.

(10) Patent No.: US 7,045,558 B2
(45) Date of Patent: May 16, 2006

(54) METHOD OF MAKING A HIGH REFRACTIVE INDEX OPTICAL MANAGEMENT COATING AND THE COATING

(75) Inventors: Bret Ja Chisholm, Clifton Park, NY (US); James Edward Pickett, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 177 days.

(21) Appl. No.: 10/650,972

(22) Filed: Aug. 29, 2003

(65) Prior Publication Data
US 2005/0049325 A1  Mar. 3, 2005

(51) Int. Cl.
*C08F 2/26* (2006.01)
*C09K 19/04* (2006.01)
*G02B 5/00* (2006.01)
*B29D 11/00* (2006.01)

(52) U.S. Cl. .................... 522/182; 522/178; 522/184; 522/134; 522/135; 522/136; 522/138; 522/141; 522/143; 522/144; 522/142; 522/168; 522/167; 522/180; 428/1.1; 359/642; 359/831; 359/838; 264/1.1; 264/1.24; 264/1.27; 264/1.31; 264/1.32; 264/1.34; 264/1.35; 264/1.38; 264/1.7; 252/582; 252/182.1; 252/182.15; 252/182

(58) Field of Classification Search ............... 522/134, 522/135, 136, 138, 141, 143, 146, 168, 169; 522/178, 180, 182, 184, 187, 144, 167, 142; 428/1.1; 359/642, 831, 838; 264/1.1, 1.24, 264/1.27, 1.31, 1.32, 1.34, 1.35, 1.38, 1.7; 252/582, 182.1, 182.15, 182
See application file for complete search history.

(56) References Cited

U.S. PATENT DOCUMENTS

| 4,262,072 | A | * | 4/1981 | Wendling et al. ............. 430/14 |
| 4,576,850 | A | | 3/1986 | Martens |
| 4,710,557 | A | | 12/1987 | Warren |
| 4,931,521 | A | * | 6/1990 | Matsuda et al. ............. 526/285 |
| 5,470,892 | A | | 11/1995 | Gupta et al. |
| 5,855,983 | A | | 1/1999 | Williams |
| 6,368,682 | B1 | | 4/2002 | Fong |
| 6,472,488 | B1 | | 10/2002 | Caye et al. |
| 6,572,975 | B1 | | 6/2003 | Dalakos |
| 6,758,992 | B1 | * | 7/2004 | Solomon et al. ............. 264/1.6 |
| 6,833,391 | B1 | | 12/2004 | Chisholm et al. |
| 2002/0004574 | A1 | | 1/2002 | Hung et al. |
| 2003/0021565 | A1 | | 1/2003 | Khudyakov et al. |
| 2003/0113091 | A1 | | 6/2003 | Chou et al. |
| 2003/0224250 | A1 | | 12/2003 | Setthachayanon et al. |

FOREIGN PATENT DOCUMENTS

| EP | 0 759448 | 1/2002 |
| JP | 059136310 | 8/1984 |
| JP | 03153715 | 7/1991 |
| JP | 04285654 | 10/1992 |
| JP | 05287040 | 11/1993 |
| JP | 2000009901 | 1/2000 |
| SU | 687087 | 9/1925 |
| SU | 349693 | 9/1972 |
| WO | WO 98/50805 | 11/1998 |
| WO | WO 01/30933 | 5/2001 |
| WO | WO 02/051892 | 7/2002 |

OTHER PUBLICATIONS

RJM Zwiers et al., "Replication of High Precision Aspherical Lenses Using UV-Curable Coatings", Conference Location: Limburg, Netherlands, Source Published by: Elsevier Applied Science Publ., London, England and New York, NY USA, pp. 673-677, 1986.

LL Beecroft et al., "High Refractive Index Polymers for Optical Applications", J.M.S. Pure Appl. Chem., A34(4), pp. 573-586, 1997.

\* cited by examiner

*Primary Examiner*—Sanza L. McClendon
(74) *Attorney, Agent, or Firm*—Andrew I. Caruso; William E. Powell, III

(57) ABSTRACT

A radiation curable composition comprises a heterocyclic acrylate or heterocyclic methacrylate. The composition is curable to make an optical management article such as an optical management coating on a substrate. A method of making an optical management article, comprises forming a radiation curable composition comprising the heterocyclic acrylate or heterocyclic methacrylate on a substrate and curing the composition to form the optical management article.

27 Claims, 2 Drawing Sheets

METHOD OF MAKING A HIGH REFRACTIVE INDEX OPTICAL MANAGEMENT COATING AND THE COATING

BACKGROUND OF THE INVENTION

The invention relates to a high refractive index optical management coating that can be used as a light management film (LMF) in a liquid crystal display, particularly an LMF that can be applied or formed in a microstructure replication process.

Microstructure replication in resinous surfaces is of importance in diverse technical fields such as fabrication of traffic signs, in which reflectivity is provided by cube-corner embossed sheeting; the production of Fresnel ophthalmic lens elements and flexible video disks; and the fabrication of brightness enhancement or light management films for liquid crystal displays. Suitable resinous compositions for the replication of microstructures are disclosed in the patent literature. Martens, U.S. Pat. No. 4,576,850 discloses a variety of such compositions. The disclosure of this patent is herein incorporated in its entirety by reference.

Typically, UV-cured acrylate coatings on a polymer film substrate are preferred LMF's because of their fast cure time and good physical properties. However, the refractive index of most acrylate polymers is relatively low. Brominated aromatic acrylate derivatives commonly are used to increase the refractive index as described by Williams, U.S. Pat. No. 5,855,983. However, often there is a limit to how much brominated acrylate derivative can be used before other properties suffer. Typically, it is found very difficult to obtain a useful LMF with refractive index greater than 1.63 using organic materials alone.

There is a need for an optical management coating, particularly an LMF with higher refractive index to improve performance.

BRIEF DESCRIPTION OF THE INVENTION

The invention relates to acrylated derivatives of heterocyclic compounds that have high refractive indices and that can be used to make a high refractive index optical management coating such as an LMF that retains other thermomechanical properties, and adhesion to the substrates upon which such films are typically disposed. According to the invention, a radiation curable composition comprises a heterocyclic acrylate or heterocyclic methacrylate. The invention also relates to an optical management article, comprising a cured heterocyclic acrylate or heterocyclic methacrylate and to an optically coated article, comprising an optical management coating on a substrate, wherein the optical management coating comprises the cured heterocyclic acrylate or heterocyclic methacrylate.

In an embodiment, the invention is a method of making an optical management article, comprising forming a radiation curable composition comprising a heterocyclic acrylate or heterocyclic methacrylate and curing the composition to form the optical management article.

In another embodiment, the invention is a method of making an optically coated article, comprising forming a radiation curable composition comprising the heterocyclic acrylate or heterocyclic methacrylate on a substrate and curing the composition by radiation to produce the optically coated article. The method can further comprise forming a primary relief structure on the surface of a substrate; forming a replica of the primary relief from the substrate; transferring the replica of the primary relief to the surface of the optically coated article to form a replicated microstructure surface.

DETAILED DESCRIPTION OF THE INVENTION

The invention includes a composition that can be cured to an optical management coating such as an LMF used in a display apparatus. The optical management coating is a high refractive index coating that can be free of halogenated components. A polycarbonate composition as described hereinafter, can be prepared into a variety of optical articles such as an LMF that comprises a plurality of prismatic microstructures. In one embodiment, the microstructures are those described in the Martens patent. The microstructures can be provided as part of a three dimensional prismatic structure. Typically, the structure has two sides, where one side is substantially smooth and the other has a three dimensional structure, such as saw-tooth formations having tilted surfaces.

Features of the invention will become apparent from the drawings and following detailed discussion, which by way of example without limitation describe preferred embodiments of the invention.

Figure 1:
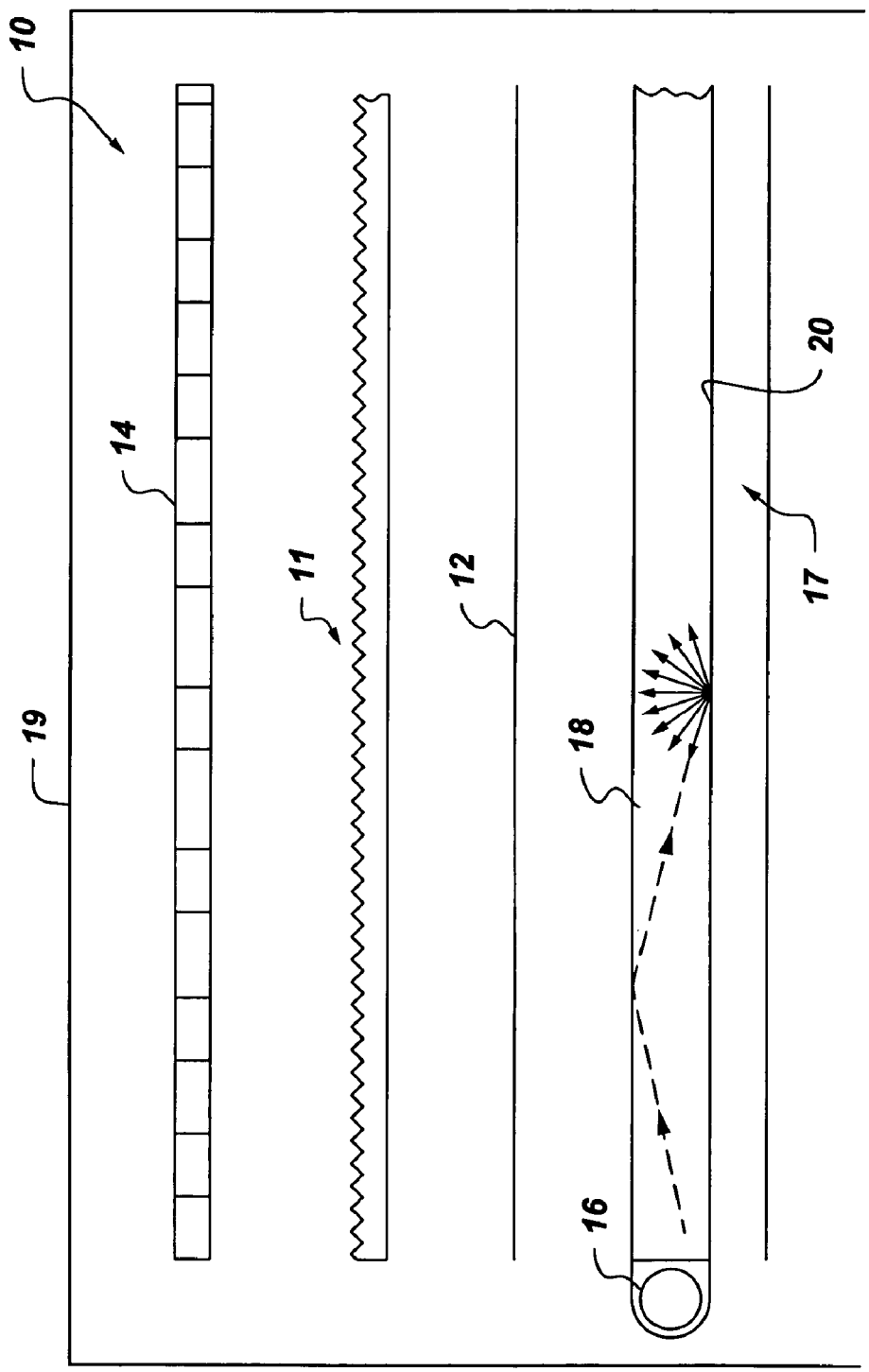
FIG. 1 is a schematic perspective view of a backlit liquid crystal display.

Referring to FIG. 1, a backlit liquid crystal display generally indicated at 10 includes an optical management article 11. The optical management article 11 is shown positioned between a diffuser 12 and a liquid crystal display panel 14. The backlit liquid crystal display also includes a light source 16 such as a fluorescent lamp, a light guide 18 for transporting light for reflection toward the liquid crystal display panel 14, and a white reflector 17 for reflecting light also toward the liquid crystal display panel 14. The optical management article 11 collimates light emitted from the light guide 18 thereby increasing the brightness of the liquid crystal display panel 14, enabling a sharper image to be produced by the liquid crystal display panel and allowing the power of the light source 16 to be reduced to produce a selected brightness. The optical management article 11 in the backlit liquid crystal display is useful in equipment such as computers, personal televisions, video recorders, mobile communication devices, and automobile and avionic instrument displays.

Figure 2:
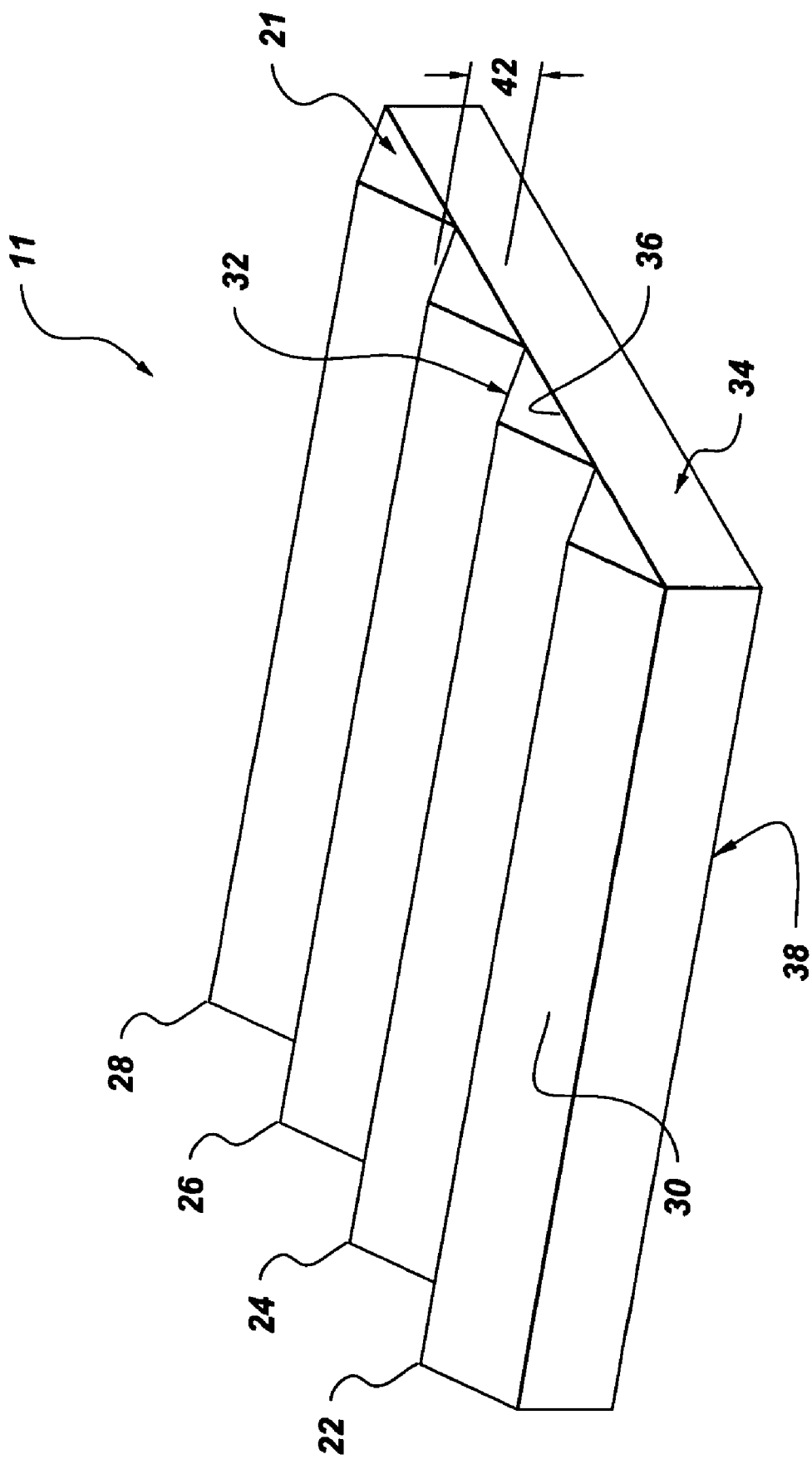
FIG. 2 is a schematic perspective view of a microstructure LMF and supporting polymeric substrate.

The optical management article 11 includes LMF 21 comprising an array of prisms typified by prisms 22, 24, 26, and 28, as illustrated in FIG. 2. Each prism, for example, has a first facet 30 and a second facet 32. The prisms 22, 24, 26, and 28 are formed on a substrate 34 that has a first surface 36 on which the prisms are formed and a second surface 38 that is substantially flat or planar and opposite the first surface.

A composition of the invention that can be cured to produce LMF 11 can include four components A, B, C, and D. Component A is at least one monofunctional liquid acrylic monomer or monmer blend and includes the heterocyclic acrylate or heterocyclic methacrylate of the invention. The heterocylic acrylate or heterocyclic methacrylate reduces viscosity of the curable composition and increases the refractive index of the cured film. An example of a monofunctional liquid acrylic monomer blend is a 50:50 mixture (by weight) of phenoxyethylacrylate and the heterocyclic acrylate of the invention, for example 2-(2-benzothiazolylthio)ethyl acrylate. The term "acrylic monomer" as used herein designates esters and amides of acrylic and methacrylic acids, the inclusion of both acids being designated by the parenthesized construction "(meth)acrylic."

Component B serves the purposes of affording improved ductility, minimizing shrinkage upon polymerization and providing improved visco-elastic properties in the cured films. It is at least one oligomeric multifunctional (meth)acrylate, usually a di(meth)acrylate. Suitable materials for component B include epoxy acrylates, urethane acrylates, polyester acrylates. Brominated epoxy acrylates are typically preferred. The brominated epoxy acrylate RDX-51027 available from UCB Chemical Inc. is an example.

The oligomeric multifunctional (meth)acrylate component B can include a molecule containing at least two (meth)acrylate functional groups. In a preferred embodiment, the multifunctional (meth)acrylate is represented by the formula (I)

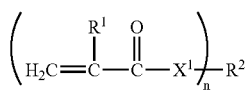

wherein $R^1$ is hydrogen or methyl; $X^1$ is O or S; $R^2$ is substituted or unsubstituted alkyl, aryl, alkaryl, arylalkyl, or heteroaryl; and n is 2, 3, or 4. Preferred $R^2$ groups include such groups as alkylene and hydroxy alkylene disubstituted bisphenol-A or bisphenol-F ethers, especially the brominated forms of bisphenol-A and -F. Suitable $R^2$ groups include those according to the formula II

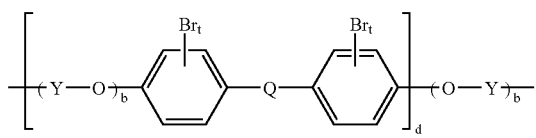

wherein Q is —C(CH$_3$)$_2$—, —CH$_2$—, —C(O)—, —S(O)—, or —S(O)$_2$—; Y is C$_1$–C$_6$ alkyl or hydroxy substituted C$_1$–C$_6$ alkyl; b is 1 to 20; t is 0, 1, 2, 3, or 4; and d is 1, 2 or 3.

The oligomeric multifunctional (meth)acrylate can include compounds produced by the reaction of an acrylic or methacrylic acid with a di-epoxide, such as bisphenol-A diglycidyl ether; bisphenol-F diglycidyl ether; tetrabromo bisphenol-A diglycidyl ether; tetrabromo bisphenol-F diglycidyl ether; 1,3-bis-{4-[1-methyl-1-(4-oxiranylmethoxy-phenyl)-ethyl]-phenoxy}-propan-2-ol; 1,3-bis-{2,6-dibromo-4-[1-(3,5-dibromo-4-oxiranylmethoxy-phenyl)-1-methyl-ethyl]-phenoxy}-propan-2-ol; and the like; and combinations thereof. Examples of such compounds include 2,2-bis(4-(2-(meth)acryloxyethoxy)phenyl)propane; 2,2-bis ((4-(meth)acryloxy)phenyl)propane; acrylic acid 3-(4-{1-[4-(3-acryloyloxy-2-hydroxy-propoxy)-3,5,-dibromo-phenyl]-1-methyl-ethyl}-2,6-dibromo-phenoxy)-2-hydroxy-propyl ester; acrylic acid 3-[4-(1-{4-[3-(4-{1-[4-(3-acryloyloxy-2-hydroxy-propoxy)-3,5-dibromo-phenyl]-1-methyl-ethyl}-2,6-dibromo-phenoxy)-2-hydroxy-propoxy]-3,5-dibromo-phenyl}-1-methyl-ethyl)-2,6-dibromo-phenoxy]-2-hydroxy-propyl ester; and the like, and combinations thereof. A suitable multifunctional (meth) acrylate based on the reaction product of tetrabrominated bisphenol-A di-epoxide is RDX 51027 available from UCB Chemicals.

In one embodiment component B comprises a urethane acrylate. Such materials can be prepared, for example, by the reaction of an alkylene diisocyanate of the formula OCN—$R^3$—NCO with a diol of the formula HO—$R^4$—OH, wherein each of $R^3$ and $R^4$ is independently a C$_{2-100}$ alkylene group, to form a urethane diol diisocyanate, followed by reaction with a hydroxyalkyl (meth)acrylate. For example, a preferred compound is a the product of reaction of an aromatic diisocyanate (e.g. TDI) with a polyester diol followed by reaction with hydroxyalkyl acrylate.

Component C is optional and includes a liquid multifunctional acrylate. Compounds suitable for use as component C include polyol poly(meth)acrylates, typically prepared from aliphatic diols, triols and/or tetraols containing 2–100 carbon atoms. Examples of suitable poly(meth)acrylates are ethylene glycol diacrylate, 1,6-hexanediol diacrylate, 2-ethyl-2-hydroxymethyl-1,3-propanediol triacrylate (trimethylolpropane triacrylate), di(trimethylolpropane) tetraacrylate, pentaerythritol tetraacrylate, the corresponding methacrylates and the (meth)acrylates of alkoxylated (usually ethoxylated) derivatives of said polyols. Also included are N,N'-alkylenebisacrylamides, particularly those containing a C$_{1-4}$ alkylene group. Particularly preferred is hexanediol diacrylate.

Component D is at least one photoinitiator effective to promote polymerization of the articles upon exposure to ultraviolet radiation. Suitable materials for use as photoinitiators are identified in the aforementioned Martens patent and in such reference works as Encyclopedia of Polymer Technology. Examples are benzoin ethers, hydroxy- and alkoxyalkyl phenyl ketones, thioalkylphenyl morpholinoalkyl ketones and acylphosphine oxides. Particularly useful in many instances is a commercially available material designated "Darocur 4265", comprising a mixture of 2-hydroxy-2-propyl phenyl ketone and (2,4,6-trimethylbenzoyl) diphenylphosphine oxide.

The curable composition includes the heterocyclic (meth) acrylate of the invention. Examples of suitable heterocyclic moieties include higher atomic weight atoms, for example sulfur, selenium, phosphorous, chlorine, bromine, iodine that contribute to the overall refractive index of the composition. Specific classes of heterocycles include benzothiazoles, benzoxazoles, cyclic sulfides, cyclic selenides, pyridines, thioxanthenes, selenoxanthenes, benzothiofurans, benzoselofurans, thiopyrans, selenopyrans, thiophenes, selenophenes, thiazoles, selenazoles, naphthothiazoles, and the like.

In one embodiment of the present invention the heterocyclic acrylic monomer is a benzothiazole having structure III

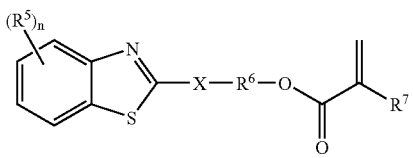

wherein $R^5$ is independently at each occurrence a $C_1$–$C_{20}$ aliphatic radical, $C_3$–$C_{30}$ cyclcoaliphatic radical, $C_4$–$C_{20}$ aromatic radical, halogen, nitro, or cyano group; n is an integer from 0–4; X is a bond, a sulfur atom, selenium atom, SO group (sulfoxide), $SO_2$ (sulfonyl group), oxygen atom, amino group, carbonyl group, or carbonyloxy group; $R^6$ is a divalent $C_1$–$C_{20}$ aliphatic radical, a divalent $C_3$–$C_{30}$ cycloaliphatic radical, a divalent $C_3$–$C_{30}$ aromatic radical; and $R^7$ is hydrogen or methyl.

As used herein the term "aliphatic radical" refers to a radical having a valence of at least one and consisting of a linear or branched array of atoms which is not cyclic. The array may include heteroatoms such as nitrogen, sulfur and oxygen or may be composed exclusively of carbon and hydrogen. Examples of aliphatic radicals include methyl, methylene, ethyl, ethylene, hexyl, hexamethylene, methoxy, ethoxy, thiomethyl, thioethyl, and the like.

In embodiment of the present invention the group $R^5$ is a aliphatic radical which is a $C_1$–$C_{20}$ alkyl thio group.

As used herein the term "cycloaliphatic radical" refers to a radical having a valance of at least one and comprising an array of atoms which is cyclic but which is not aromatic, and which does not further comprise an aromatic ring. The array may include heteroatoms such as nitrogen, sulfur and oxygen or may be composed exclusively of carbon and hydrogen. Examples of cycloaliphatic radicals include cyclopropyl, cyclopentyl cyclohexyl, 2-cyclohexylethy-1-yl, tetrahydrofuranyl and the like.

As used herein the term "aromatic radical" refers to a radical having a valence of at least one and comprising at least one aromatic ring. Examples of aromatic radicals include phenyl, pyridyl, furanyl, thienyl, naphthyl, phenylene, and biphenyl. The term includes groups containing both aromatic and aliphatic components, for example a benzyl group, a phenethyl group or a naphthylmethyl group. The term also includes groups comprising both aromatic and cycloaliphatic groups for example 4-cyclopropylphenyl and 1,2,3,4-tetrahydronaphthalen-1-yl.

2-(2-benzothiazolylthio)ethyl acrylate is a preferred heterocyclic (meth)acrylate.

In one embodiment of the invention, the composition Component B is present in an amount of about 40 to 95, desirably 60 to 80 and preferably 55 to 65 weight percent. Component A (monomeric component) is present in an amount of about 10 to 60, desirably 20 to 50 and preferably 35 to 45 weight percent. Optional Component C is present in an amount corresponding to 0 to less than about 30, desirably 7 to 20 and preferably 8 to 15 percent by weight of the composition. Component D, the photoinitiator, is typically present in an amount corresponding to about 0.0001 to 5 weight percent of the composition.

Any suitable supporting substrate may be employed to support the optical management coating according to the present invention, provided its use can produce an article which is transparent to visible light. Among the particularly useful resins of this type are thermoplastics such as poly (methyl methacrylate), poly(ethylene terephthalate) (PET), poly(ethylene naphthaleneate) (PEN), and aromatic polycarbonates, especially bisphenol A polycarbonate; that is, the polycarbonate derived from 2,2-bis(4-hydroxyphenyl)propane. Bisphenol A homopolycarbonate is especially preferred. In one embodiment, the supporting substrate 34 in FIG. 2 is a thermoset material. The thermoset material may be one of an epoxy, a cross-linked acrylic, a polyester, a melamine, and a silicone resin. A preferred coated structure comprises a an aromatic polycarbonate substrate, and a microstructured resinous layer comprising the cured heterocylic acrylic compositions described herein.

Advantageously, the compositions of the invention have optimum physical properties for retention of the optical microstructure. These properties include viscoelastic properties such as modulus, and glass transition temperature (Tg) appropriate for retention of shape and dimensions of the optical microstructure, and overall film integrity during handling, use and storage. Typically, the cured composition will have a Tg of at least 40°, desirably at least 50°, and preferably at least 60°.

The process to form a replicated microstructure on a substrate coated with the composition of the invention is illustrated as follows. First, a radiation curable composition according to the invention is deposited onto a surface of a transparent substrate, which is typically polycarbonate. The curable composition is contacted with a mold comprising a "negative" of a desired optical microstructure. The composition is irradiated to cure the radiation curable composition to form a composite comprising the substrate and a replicated cured composition. The mold is then separated from the cured composite to provide an LMF.

The optically coated article of the invention is characterized by a surface with replicated microstructure comprising a plurality of utilitarian discontinuities, such as projections and depressions. The surface can be readily released from a mold after radiation curing. The article surface retains molded detail and retains detail replication under a wide variety of conditions. The article has a variety of desired properties, such as toughness, flexibility, optical clarity and homogeneity and resistance to common solvents. The article microstructure has a high thermal dimensional stability, resistance to abrasion and impact, and integrity even when the article is bent to an angle as great as 180°.

The following Examples are illustrative and should not be construed as a limitation on the scope of the claims unless a limitation is specifically recited.

EXAMPLE 1

Synthesis of 2-(2-benzothiazolylthio)ethyl acrylate

Step 1. Preparation of 2-(2-benzotbiazolylthio)ethanol

2-Mercaptobenzothiazole (100 mmol, 16.7 g), ethylene carbonate (100 mmol, 8.8 g), potassium carbonate (0.7 mmol; 0.1 g) and 30 mL of toluene were placed in a 250 mL round bottomed flask equipped with a reflux condenser and a magnetic stir bar. The mixture was stirred and heated to reflux temperature for 1.5 hours whereupon thin layer chromatography (silica gel; 10% ethanol in chloroform eluent) indicated that the reaction was essentially complete. The solution was cooled to room temperature. Upon seeding with authentic product, an approximately 50% yield of essentially pure product could be obtained. However, the reaction mixture can be taken to the next step without purification.

Step 2. Preparation of the Acrylate Ester 2-(2-benzothiazolylthio)ethanol (100 mmol, 21.1 g), a total of 100 mL of toluene, potassium carbonate (250 mmol, 34.5 g), and tetrabutyl ammonium bromide (1 mmol, 0.32 g) were combined in a 500 mL round bottomed flask equipped with a reflux condenser and magnetic stir bar. Acryloyl chloride (200 mmol, 18.1 g, 16.2 mL) was added in portions over the course of about 1 hour. An exotherm ensued raising the temperature of the reaction mixture to about 55° C. The reaction mixture was allowed to cool back to room temperature over the course of about 8 hours. Thin layer chromatography indicated that the reaction was essentially complete. After sitting overnight, the solid inorganic residue was filtered and washed with additional toluene. The combined toluene filtrate was then washed with two 50 mL portions of deionized water in a separatory funnel followed by a wash with saturated sodium chloride solution. The organic layer was filtered through silica gel and evaporated under reduced pressure to give a pale yellow oil. NMR spectroscopy showed it to be primarily 2-(2-benzothiazolylthio)ethyl acrylate. The refractive index of this material was 1.63.

EXAMPLE 2

The procedure of Example 1 was followed using 6-ethoxy-2-mercaptobenzothiazole as a starting material to produce 2-(2-(6-ethoxybenzothiazolyl)thio)ethyl acrylate as a colorless oil with refractive index of 1.61.

EXAMPLE 3

A mixture was prepared consisting of 1.06 g of 2-(2-benzothiazolylthio)ethyl acrylate prepared as described in Example 1, 0.40 g of RDX51027 brominated BPA diacrylate oligomer (product of UCB) and 0.04 g of Darocur 4265 photoinitiator which is a 50/50 mixture of 2,4,6-trimethylbenzoyl-diphenyl-phosphineoxide and 2-hydroxy-2-methyl-1-phenyl-propan-1-one (product of Ciba Specialty Chemicals). The solution was spin coated onto a silicon wafer using a speed of 750 rpm and a spin time of 20 seconds. The coated specimen was cured with a Fusion UV Systems process Model DRS-120 using 3 passes under the H bulb in a nitrogen atmosphere. The lamp to sample distance was 2.1 inches and the belt speed was 10 ft./min.

The refractive index of the film was determined on a Metricon prism coupling instrument at 632.8 nm. The average of three determinations was 1.652.

EXAMPLE 4

A coating formulation consisting of 5.00 g of 2-(2-benzothiazolylthio)ethyl acrylate, 7.5 g of RDX51027, and 0.0632 g of Irgacure 819 bis(2,4,6-trimethylbenzoyl)-phenylphosphineoxide (product of Ciba Specialty Chemicals) was prepared. The mixture was applied to a 10 mil Lexan® polycarbonate film and pressed against a flat plate. The coated film was placed film side up and cured as described in Example 2.

Color of the coated film was determined on a GretagMacbeth 7000A calorimeter (D65 illuminant 10D observer); transmission and haze were determined on a BYK Gardner Hazegard plus; adhesion of the coating to the substrate was determined by a scribed tape pull according to ASTM D3359 (5B indicates no adhesion failure). Results are shown in the TABLE below.

TABLE

| Film | L | a | b | YID | % Trans. | % Haze | adhesion |
|---|---|---|---|---|---|---|---|
| PC blank | 96.0 | 0.0 | 0.3 | 0.5 | 93.1 | 0.17 | |
| film #1 (thin) | 95.7 | 0.0 | 0.5 | 0.8 | 92.4 | 0.66 | 5B |
| film #2 (thick) | 95.7 | −0.1 | 0.7 | 1.1 | 92.3 | 0.68 | 5B |

Color, haze, and adhesion were excellent.

EXAMPLE 5

A coating containing 50 weight percent 2-(2-benzothiazolylthio)ethyl acrylate, 49.5 weight percent RDX 51027, and 0.5 weight percent Irgacure 819 was used to produce a brightness enhancement film by pouring coating on to a metal mold containing a prismatic structure, placing a film of polycarbonate on top of the liquid, spreading the liquid between the mold and polycarbonate using a lamination process, and curing the coating with UV light by passing the entire composite structure through a UV processor with the backside of the polycarbonate substrate facing the UV light source. Once cured, the coating, which was adhered to the polycarbonate substrate, was peeled from the mold producing the brightness enhancing film.

The laminating process employed the use of a laminator consisting of two rubber rolls: a bottom variable speed drive roll and a pneumatically driven top nip roll. This system is used to press together laminate stacks that are passed between the rolls. Curing was accomplished with a Fusion UV Systems process Model DRS-120 using a single pass under the V bulb using lamp to sample distance of 2.1 inches and a belt speed of 10 ft./min.

The geometry of the prisms on the mold can be found in FIG. 6 of the copending U.S. application Ser. No. 10/065,981 entitled "Brightness Enhancement Film With Improved View Angle" filed Dec. 6, 2002, which is incorporated herein in its entirety.

The brightness of the coated cured microstructured films was determined using the Display Analysis system Microvision SS220. Microvision SS220, a computer based measurement system, uses a goniometric assembly and a mechanical positioner for the collection of in-axis and off-axis data at various locations of the films. The brightness measurements are achieved by utilizing a diffraction grating spectrometer with a collimation optical probe. The microstructured or light management film is mounted on a LG-Phillips backlight module, which is composed of a bottom diffuser D177 and crossed light management films. A 13 point test and hemi test are conducted to provide the uniformity of the brightness over 13 specific locations on the film and the range of viewing angle at the center location of the film. The brightness is provided in units of candela per meter squared ($cd/m^2$).

The brightness of the film produced was 1,135 $cd/m^2$.

While preferred embodiments of the invention have been described, the present invention is capable of variation and modification and therefore should not be limited to the precise details of the Examples. The invention includes changes and alterations that fall within the purview of the following claims.

What is claimed is:

1. A radiation curable optical coating composition, comprising an acrylated benzothiazole or methacrylated benzothiazole having structure III

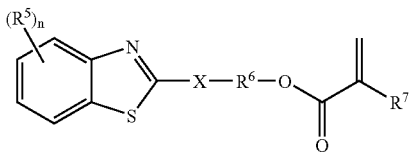

wherein $R^5$ is independently at each occurrence a $C_1$–$C_{20}$ aliphatic radical, $C_3$–$C_{30}$ cyclcoaliphatic radical, $C_4$–$C_{20}$ aromatic radical, halogen, nitro, or cyano group; n is an integer from 0–4; X is a bond, a sulfur atom, selenium atom, $SO$ group (sulfoxide), $SO_2$ (sulfonyl group), oxygen atom, amino group, carbonyl group, or carbonyloxy group; $R^6$ is a divalent $C_1$–$C_{20}$ aliphatic radical, a divalent $C_3$–$C_{30}$ cycloaliphatic radical, a divalent $C_3$–$C_{30}$ aromatic radical; and $R^7$ is hydrogen or methyl.

2. The radiation curable composition of claim 1, which composition is radiation curable to an optical management article having a surface with a replicated microstructure having a plurality of utilitarian discontinuities for an optical purpose.

3. The radiation curable composition of claim 1, which composition is radiation curable to an optical management coating.

4. The radiation curable composition of claim 1, which composition is radiation curable to a light management film.

5. The composition of claim 1, wherein the acrylated benzothiazole or methacrylated benzothiazole III comprises a higher atomic weight atom selected from the group consisting of sulfur, selenium, phosphorous, chlorine, bromine and iodine.

6. The composition of claim 1, comprising 2-(2-benzothiazolylthio)ethyl acrylate.

7. The composition of claim 1, which composition is radiation curable to an optical resinous article having a glass transition temperature of at least 40° C.

8. The composition of claim 1, comprising (A) the acrylated benzothiazole or methacrylated benzothiazole; and further comprising (B) a multifunctional (meth)acrylate; an optional (C) liquid, multifunctional (meth)acrylate; and (D) a photoinitiator.

9. The composition of claim 8, comprising 10 to 60 weight percent (A) the acrylated benzothiazole or methacrylated benzothiazole; 40 to 95 weight percent (B) a multifunctional (meth)acrylate; 0 to less than about 30 weight percent (C) a liquid, multifunctional (meth)acrylate; and 0.0001 to 5 weight percent (D) a photoinitiator.

10. The composition of claim 8, comprising 20 to 50 weight percent (A) the acrylated benzothiazole or methacrylated benzothiazole; 60 to 80 weight percent (B) a multifunctional (meth)acrylate; 7 to 20 weight percent (C) a liquid, multifunctional (meth)acrylate; and 0.0001 to 5 weight percent (D) a photoinitiator.

11. The composition of claim 8, comprising 35 to 45 weight percent (A) the acrylated benzothiazole or methacrylated benzothiazole; 55 to 65 weight percent (B) a multifunctional (meth)acrylate; 8 to 15 weight percent (C) a liquid, multifunctional (meth)acrylate and 0.0001 to 5 weight percent (D) a photoinitiator.

12. An optical management article comprising a radiation curable optical coating composition, comprising an acrylated benzothiazole or a methacrylated benzothiazole.

13. The optical management article of claim 12, comprising a surface with a replicated microstructure having a plurality of utilitarian discontinuities for an optical purpose.

14. The optical management article of claim 12, wherein the article is an optical management coating.

15. The optical management article of claim 12, wherein the article is a light management film.

16. The optical management article of claim 12, wherein the acylated benzothiazole or methacrylated benzothiazole comprises 2-(2-benzothiazolythio)ethyl acrylate.

17. The optical management article of claim 12, having a glass transition temperature of at least 40° C.

18. A method of making an optical management article, comprising forming a radiation curable optical coating composition comprising an acrylated benzothiazole or methacrylated benzothiazole and curing the composition to form the optical management article.

19. An optically coated article, comprising an optical management coating on a substrate, wherein the optical management coating comprises a acrylated benzothiazole or methacrylated benzothiazole.

20. The optically coated article of claim 19, wherein the optical management coating has a surface with a replicated microstructure having a plurality of utilitarian discontinuities for an optical purpose.

21. The optically coated article of claim 19, wherein the optical management coating is a light management film.

22. The optically coated article of claim 19, wherein the acrylated benzothiazole or methacrylated benzothiazole is 2-(2-benzothiazolylthio)ethyl (meth)acrylate.

23. The optically coated article of claim 19, wherein the optical management coating has a glass transition temperature of at least 40° C.

24. The optically coated article of claim 19, wherein the substrate is a polymethyl methacrylate, an aromatic polycarbonate, polyethylene terephthalate or a thermoset.

25. The optically coated article of claim 19, wherein the substrate is derived from 2,2-bis(4-hydroxyphenyl)propane.

26. The optically coated article of claim 19, wherein the substrate is a thermoset selected from the group consisting of an epoxy, a cross-linked acrylic, a polyester, a melamine, and a silicone.

27. A method of making an optically coated article, comprising forming a layer of a radiation curable optical coating composition comprising a acrylated benzothiazole or methacrylated benzothiazole on a substrate and curing the composition by radiation to produce the optically coated article.

* * * * *